(12) United States Patent
Yamamoto et al.

(10) Patent No.: US 11,130,831 B2
(45) Date of Patent: Sep. 28, 2021

(54) CURABLE COMPOSITION, FILM, CURED PRODUCT, AND MEDICAL MEMBER

(71) Applicant: FUJIFILM Corporation, Tokyo (JP)

(72) Inventors: Yosuke Yamamoto, Minamiashigara (JP); Yuta Shigenoi, Minamiashigara (JP); Atsushi Sugasaki, Minamiashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/835,738

(22) Filed: Mar. 31, 2020

(65) Prior Publication Data

US 2020/0270384 A1 Aug. 27, 2020

Related U.S. Application Data

(63) Continuation of application No. PCT/JP2018/037287, filed on Oct. 4, 2018.

(30) Foreign Application Priority Data

Oct. 18, 2017 (JP) .............................. JP2017-201929

(51) Int. Cl.
| | | |
|---|---|---|
| *C08F 220/36* | (2006.01) | |
| *C08F 220/38* | (2006.01) | |
| *A61L 27/34* | (2006.01) | |
| *C08F 220/56* | (2006.01) | |

(52) U.S. Cl.
CPC .......... *C08F 220/365* (2020.02); *A61L 27/34* (2013.01); *C08F 220/387* (2020.02); *C08F 220/56* (2013.01)

(58) Field of Classification Search
USPC .......................... 526/301, 287, 302; 560/196
See application file for complete search history.

(56) References Cited

U.S. PATENT DOCUMENTS

| | | |
|---|---|---|
| 2008/0262181 A1 | 10/2008 | Kitano et al. |
| 2017/0009069 A1 | 1/2017 | Jiang et al. |
| 2017/0226251 A1 | 8/2017 | Fukagawa |
| 2018/0142119 A1 | 5/2018 | Fukagawa |
| 2018/0215925 A1 | 8/2018 | Hatanaka |
| 2018/0360696 A1 | 12/2018 | Nojiri et al. |
| 2019/0002727 A1 | 1/2019 | Hiroi et al. |
| 2020/0223967 A1* | 7/2020 | Yamamoto ................ C08J 5/18 |

FOREIGN PATENT DOCUMENTS

| | | |
|---|---|---|
| CA | 2709379 A1 | 7/2009 |
| CN | 103880714 A | 6/2014 |
| DE | 1211156 B | 2/1966 |
| EP | 1363346 A2 | 11/2003 |
| EP | 2339401 A1 | 6/2011 |
| EP | 2339402 A1 | 6/2011 |
| JP | 2004091690 A | 3/2004 |
| JP | 2005142077 A | 6/2005 |
| JP | 2009198868 A | 9/2009 |
| JP | 2012-31400 A | 2/2012 |
| JP | 2017105716 A | 6/2017 |
| WO | 2005113620 A1 | 12/2005 |
| WO | 2011/025847 A2 | 3/2011 |
| WO | 2016067795 A1 | 5/2016 |
| WO | 2016/149488 A1 | 9/2016 |
| WO | 2016196633 A1 | 12/2016 |
| WO | 2017006850 A1 | 1/2017 |
| WO | 2017018146 A1 | 2/2017 |
| WO | 2017/073437 A1 | 5/2017 |
| WO | 2017098724 A1 | 6/2017 |

OTHER PUBLICATIONS

Zhang, Lei et al., "Zwitterionic hydrogels implanted in mice resist the foreign-body reaction", Nature Biotechnology, May 12, 2013, vol. 31, No. 6, pp. 553-557 (6 pages).
International Search Report dated Oct. 30, 2018 from the International Searching Authority in International Application No. PCT/JP2018/037287.
International Preliminary Report on Patentability dated Apr. 21, 2020 from the International Bureau in International Application No. PCT/JP2018/037287.
Written Opinion dated Oct. 30, 2018 from the International Bureau in International Application No. PCT/JP2018/037287.
Sebastian Hahnel et al., "Surface properties and in vitro *Streptococcus mutans* adhesion to dental resin polymers", Journal of Materials Science: Materials in Medicine, vol. 19, No. 7, Jan. 16, 2018, pp. 2619-2627 (9 pages total).

(Continued)

*Primary Examiner* — Fred M Teskin
(74) *Attorney, Agent, or Firm* — Sughrue Mion, PLLC

(57) ABSTRACT

A curable composition contains one or more betaine monomers selected from the group consisting of a compound represented by Formula (1) and a compound represented by Formula (2).

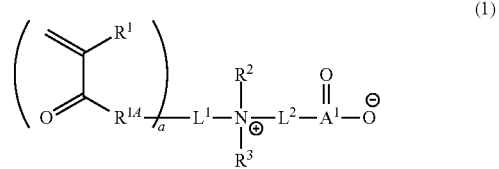

(1)

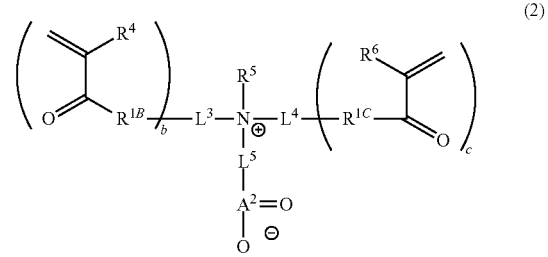

(2)

10 Claims, No Drawings

(56) References Cited

OTHER PUBLICATIONS

Mary Beth Browning et al., "Development of a Biostable Replacement for PEGDA Hydrogels", Biomacromolecules, vol. 13, No. 3, 2012, pp. 779-786 (8 pages total) Feb. 22, 2012.
Norbert Moszner et al., "Monomers for adhesive polymers, 4$^a$ Synthesis and radical polymerization of hydrolytically stable crosslinking monomers", Macromolecular Materials and Engineering, vol. 288, No. 8, Aug. 1, 2003, pp. 621-628 (8 pages total).
Izabela M. Barszczewska-Rybarek, "Characterization of urethane-dimethacrylate derivatives as alternative monomers for the restorative composite matrix", Dental Materials, vol. 30 No. 12, Oct. 18, 2014, pp. 1336-1344 (9 pages total).
Communication dated Aug. 21, 2020, from the European Patent Office in European Application No. 18868285.0.
Communication dated Mar. 30, 2021, from the European Patent Office in European Application No. 18868285.0.
Xueping Ge et al., "Synthesis and Evaluation of a Novel Co-Initiator for Dentin Adhesives Polymerization Kinetics and Leachables Study", Jom: Journal of Metals, vol. 67, No. 4, 2015, pp. 796-803 (8 pages total).
Office Action dated Jun. 22, 2021 from The State Intellectual Property Office of P.R. of China in Application No. 201880063324.6.

\* cited by examiner

CURABLE COMPOSITION, FILM, CURED PRODUCT, AND MEDICAL MEMBER

CROSS-REFERENCE TO RELATED APPLICATIONS

This application is a Continuation of PCT International Application No. PCT/JP2018/037287 filed on Oct. 4, 2018, which claims priority under 35 U.S.C. § 119(a) to Japanese Patent Application No. 2017-201929 filed on Oct. 18, 2017. Each of the above application(s) is hereby expressly incorporated by reference, in its entirety, into the present application.

BACKGROUND OF THE INVENTION

1. Field of the Invention

The present invention relates to a curable composition, a film, a cured product, and a medical member.

2. Description of the Related Art

Originally, it is desired that artificial organs, medical instruments, and the like are made of a material which is compatible with a substance constituting a living body and is hardly contaminated. For example, it is desired that artificial blood vessels, catheters, stents, artificial bones, and dentures that are introduced into a human body for a long period of time do not cause an inflammatory response and rejection. In addition, the replacement of those artificial organs or medical instruments caused by contamination imposes a burden on the patient. Therefore, it is desired that artificial organs, medical instruments, and the like are formed of a material which hardly interacts with biological materials such as proteins, blood cells, and cells. That is, it is desired that artificial organs, medical instruments, and the like are formed of a material difficult for the aforementioned biological materials to be attached (adhere).

For example, WO2016/067795A discloses "a material nonadhesive to biological materials containing a polymer compound (A) containing a repeating unit derived from a sulfobetaine monomer having a predetermined structure". Examples in WO2016/067795A specifically disclose a curable composition containing a sulfobetaine monomer having the aforementioned predetermined structure and a (meth) acrylate-based monomer or N-[tris(3-acrylamidopropoxymethyl)methyl] acrylamide as a crosslinking agent and a cured product of the curable composition (material nonadhesive to biological materials).

SUMMARY OF THE INVENTION

The cured product (material nonadhesive to biological materials) is also required to have excellent substrate adhesion. In the living body, artificial organs, medical instruments, and the like are generally used in a situation where these contact body fluids (for example, saliva, blood, and the like), which contain water as a main component, with high frequency. Therefore, "have excellent substrate adhesion" mentioned herein means that even after a substrate with a film, which includes a substrate and a film formed on the substrate, is immersed in an aqueous liquid, the film is not peeled or hardly peeled from the substrate. Examples of the substrate include medical instruments such as artificial blood vessels, catheters, stents, artificial bones, and dentures.

The inventors of the present invention prepared the curable composition described in Examples in WO2016/067795A and examined the physical properties of the cured product. As a result, it has been revealed that the cured product does not necessarily satisfy the currently required level of substrate adhesion, and needs to be further improved.

Therefore, an object of the present invention is to provide a curable composition capable of providing a cured product having excellent substrate adhesion and excellent biocompatibility.

Another object of the present invention is to provide a cured product and a film having excellent substrate adhesion and excellent biocompatibility.

Another object of the present invention is to provide a medical member comprising the cured product.

In order to achieve the above objects, the inventors of the present invention conducted intensive studies. As a result, the inventors have found that the above objects can be achieved in a case where the curable composition contains a betaine monomer having a predetermined structure, and have accomplished the present invention.

That is, the inventors have found that the above objects can be achieved by the following constitution.

[1] A curable composition containing one or more betaine monomers selected from the group consisting of a compound represented by Formula (1) which will be described later and a compound represented by Formula (2) which will be described later.

[2] The curable composition described in [1], in which $A^1$ in Formula (1) represents S=O, and $A^2$ in Formula (2) represents S=O.

[3] The curable composition described [1] or [2], further containing one or more monomers selected from the group consisting of a compound represented by Formula (A1) which will be described later and a compound represented by Formula (A2) which will be described later.

[4] A film containing a polymer compound containing one or more repeating units selected from the group consisting of a repeating unit derived from a compound represented by Formula (1) which will be described later and a repeating unit derived from a compound represented by Formula (2) which will be described later.

[5] A cured product formed by curing the curable composition described in any one of [1] to [3].

[6] The cured product described in [5] that is in the form of a film.

[7] The cured product described in [5] or [6] that is used as a biomaterial.

[8] A medical member containing a substrate and the cured product described in any one of [5] to [7] disposed on the substrate.

[9] A compound represented by Formula (1) which will be described later.

[10] A compound represented by Formula (2) which will be described later.

According to the present invention, it is possible to provide a curable composition capable of providing a cured product having excellent substrate adhesion and excellent biocompatibility.

Furthermore, according to the present invention, it is possible to provide a cured product and a film having excellent substrate adhesion and excellent biocompatibility.

In addition, according to the present invention, it is possible to provide a medical member comprising the cured product.

DESCRIPTION OF THE PREFERRED EMBODIMENTS

Hereinafter, the present invention will be specifically described.

The following constituents will be described based on the typical embodiments of the present invention in some cases, but the present invention is not limited to the embodiments.

In the present specification, a range of numerical values described using "to" means a range including numerical values listed before and after "to" as a lower limit and an upper limit.

In the present specification, "(meth)acrylamide" has a concept including either or both of the acrylamide and methacrylamide. The same is true of the terms such as "(meth)acryl", "(meth)acrylate", and "(meth)acryloyl".

In the present specification, in a case where there is a plurality of substituents, linking groups, and the like (hereinafter, described as substituents and the like) marked with specific reference signs, or in a case where a plurality of substituents and the like are simultaneously specified, the substituents and the like may be the same as or different from each other. The same is true of a case where the number of substituents and the like is specified.

Furthermore, in the present specification, in a case where there is no description regarding whether or not a group (atomic group) is substituted or unsubstituted, the group includes both the group having no substituent and group having a substituent. For example, "alkyl group" includes not only an alkyl group having no substituent (unsubstituted alkyl group) but also an alkyl group having a substituent (substituted alkyl group).

In the present specification, "biological material" is a term that means a wide variety of materials including materials constituting the living body and materials involved in the living body. For example, the term means materials includes proteins, cells, tissues which is a group of cells, peptides, vitamins, hormones, blood cells, antigens, antibodies, bacteria, viruses, and the like.

Furthermore, in the present specification, the term "properties of inhibiting the adhesion of biological materials" means the properties of perfectly preventing adhesion and also suppressing adhesion (reducing adhesion) before and after application even though adhesion occurs. Therefore, the term has a concept including not only the prevention of adhesion but also the inhibition of adhesion.

[Curable Composition]

One of the characteristics of the curable composition according to an embodiment of the present invention (hereinafter, referred to as "the composition according to the embodiment of the present invention" as well) is that the curable composition contains one or more betaine monomers (hereinafter, referred to as "specific betaine monomer" as well) selected from the group consisting of a compound represented by Formula (1) which will be described later and a compound represented by Formula (2) which will be described later.

The specific betaine monomer contains two or more polymerizable groups and a urethane bond or a urea bond. Presumably, this structure may contribute to the improvement of the substrate adhesion. More specifically, because the specific betaine monomer has two or more polymerizable groups, a film formed of the specific betaine monomer has an excellent crosslinking density (in other words, a high crosslinking density). In addition, because the specific betaine monomer contains a hydrogen bonding group called urethane bond or urea bond, the film formed of the specific betaine monomer becomes a dense film formed by the formation of intermolecular hydrogen bonding through the hydrogen bonding group. Presumably, as a result of the synergy between these mechanisms of action, even in a case where a substrate with a film, which includes a substrate and a film formed on the substrate, is immersed in an aqueous liquid, the aqueous liquid may be inhibited from permeating the interface between the substrate and the film.

The specific betaine monomer exhibits excellent biocompatibility due to a betaine moiety in the compound.

Hereinafter, each of the components contained in the composition according to the embodiment of the present invention will be specifically described.

[Specific Betaine Monomer]

The composition according to the embodiment of the present invention contains one or more betaine monomers selected from the group consisting of a compound represented by Formula (1) and a compound represented by Formula (2). Generally, betaine refers to a compound (inner salt) which has a positive charge and a negative charge at non-adjacent positions in the same molecule but does not carry a charge as a whole molecule, in which a hydrogen atom is not bonded to an atom having a positive charge.

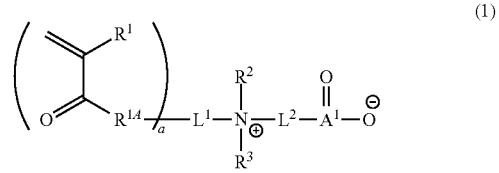

(1)

In Formula (C), $R^1$ represents a hydrogen atom or an alkyl group.

The number of carbon atoms in the alkyl group represented by $R^1$ is not particularly limited, but is preferably 1 to 15, more preferably 1 to 10, even more preferably 1 to 6, and particularly preferably 1 to 3. The alkyl group may be linear, branched, or cyclic.

Examples of the alkyl group include a methyl group, an ethyl group, a n-propyl group, an isopropyl group, a n-butyl group, a t-butyl group, a n-hexyl group, a cyclopentyl group, a cyclohexyl group, and the like.

The alkyl group may have a substituent. The substituent that the alkyl group can have is not particularly limited, and examples thereof include a substituent W which will be described later.

As $R^1$, particularly, a hydrogen atom or an alkyl group having 1 to 6 carbon atoms is preferable, and a hydrogen atom or an alkyl group having 1 to 3 carbon atoms is more preferable.

$R^2$ and $R^3$ each independently represent an alkyl group.

The alkyl group represented by $R^2$ and $R^3$ has the same definition as the alkyl group represented by $R^1$, and the suitable embodiments thereof are also the same.

$R^{1A}$ represents an oxygen atom or $NR^{101}$.

$R^{101}$ represents a hydrogen atom or an alkyl group. The alkyl group represented by $R^{101}$ has the same definition as the alkyl group represented by $R^1$, and the suitable embodiments thereof are also the same. As $R^{101}$, a hydrogen atom is preferable.

a represents an integer of 2 to 6.

In view of further improving the substrate adhesion, a is preferably 2 to 4, and more preferably 2 or 3.

$L^1$ represents an (a+1)-valent aliphatic hydrocarbon group which contains a urethane bond (—NH—CO—O— or —O—CO—NH—) or a urea bond (—NH—CO—NH—) and may contain —O—. That is, $L^1$ is linked to a pieces of monovalent group represented by Formula (X) and a nitrogen atom (cationized nitrogen atom) specified in Formula (1).

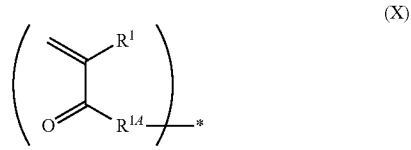

In Formula (X), $R^1$ and $R^{1A}$ have the same definitions as $R^1$ and $R^{1A}$ in Formula (1). * represents a position linked to $L^1$.

The number of carbon atoms in the aliphatic hydrocarbon group represented by $L^1$ is not particularly limited, but is, for example, 1 to 30, preferably 1 to 20, more preferably 1 to 15, and even more preferably 1 to 12.

Furthermore, the aliphatic hydrocarbon group may have a substituent. The substituent that the aliphatic hydrocarbon group can have is not particularly limited, and examples thereof include a substituent W which will be described later.

In $L^1$, a carbon atom is usually located at a position adjacent to a nitrogen atom (cationized nitrogen atom) specified in the chemical formula and at a position adjacent to $R^{1A}$.

Examples of $L^1$ include a linking group represented by Formula (1A-1) or a linking group represented by Formula (1A-2).

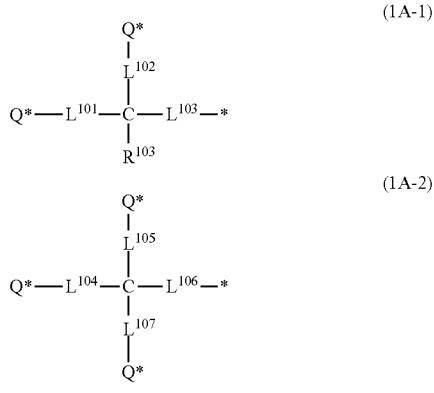

In Formula (1A-1), $R^{103}$ represents a hydrogen atom or a substituent. The substituent is not particularly limited, and examples thereof include the substituent W which will be described later.

In the formulas (1A-1) to (1A-2), $L^{101}$ to $L^{107}$ each represent a single bond or an alkylene group which may contain —O—, a urethane bond, or a urea bond.

In Formula (1A-1), at least one or more groups among $L^{101}$ to $L^{103}$ represent an alkylene group which contains a urethane bond or a urea bond and may contain —O—. In Formula (1A-2), one or more groups among $L^{104}$ to $L^{107}$ represent an alkylene group which contains a urethane bond or a urea bond and may contain —O—.

The number of carbon atoms in the alkylene group, which is represented by $L^{101}$ to $L^{107}$ and may contain —O—, a urethane bond, or a urea bond, is not particularly limited, but is preferably 1 to 12, more preferably 1 to 6, and even more preferably 1 to 3. In addition, the alkylene group which is represented by $L^{101}$ to $L^{107}$ and may contain —O—, a urethane bond, or a urea bond may be linear, branched, or cyclic.

Q* represents a position linked to the monovalent group represented by Formula (X), and * represents a position linked to a nitrogen atom (cationized nitrogen atom) specified in Formula (1).

$L^{101}$ to $L^{107}$ may further have a substituent. The substituent is not particularly limited, and examples thereof include the substituent W which will be described later. In $L^{101}$ to $L^{107}$, a carbon atom is usually located at a position linked to Q* or a position linked to a nitrogen atom (cationized nitrogen atom) specified in Formula (1).

$L^2$ represents an alkylene group which may contain —O—, —NR$^{104}$—, —CO—, or a divalent linking group obtained by combining these.

$R^{104}$ represents a hydrogen atom or a substituent. The substituent represented by $R^{104}$ is not particularly limited, and examples thereof include the substituent W which will be described later. Among these, a hydrogen atom is preferable as $R^{104}$.

The number of carbon atoms in the alkylene group, which is represented by $L^2$ and may contain —O—, —NR$^{104}$—, —CO— or a divalent linking group obtained by combining these, is not particularly limited. For example, the number of carbon atoms in the alkylene group is 1 to 30, preferably 1 to 20, more preferably 1 to 15, and even more preferably 1 to 12.

In $L^2$, a carbon atom is usually located at a position adjacent to a nitrogen atom (cationized nitrogen atom) specified in the chemical formula.

Furthermore, the alkylene group may have a substituent. The substituent that the alkylene group, which is represented by $L^2$ and may contain —O—, —NR$^{104}$—, —CO—, or a divalent linking group obtained by combining these, is not particularly limited, and examples of the substituent include the substituent W which will be described later.

$A^1$ represents S=O or a carbon atom. In view of further improving the biocompatibility, $A^1$ is preferably S=O.

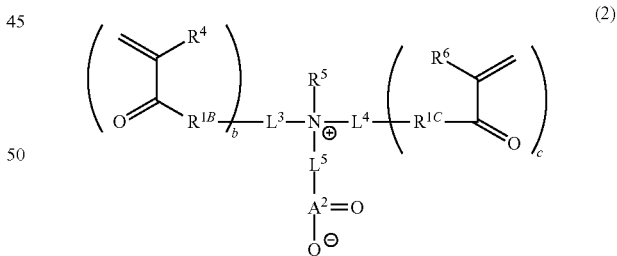

In Formula (2), $R^4$ and $R^6$ each independently represent a hydrogen atom or an alkyl group. The alkyl group represented by $R^4$ and $R^6$ has the same definition as the alkyl group represented by $R^1$ in Formula (1), and the suitable embodiments thereof are also the same. As $R^4$ and $R^6$, particularly, a hydrogen atom or an alkyl group having 1 to 6 carbon atoms is preferable, and a hydrogen atom or an alkyl group having 1 to 3 carbon atoms is more preferable.

$R^5$ represents an alkyl group. The alkyl group represented by $R^5$ has the same definition as the alkyl group represented by $R^2$ and $R^3$ in Formula (1), and the suitable embodiments thereof are also the same.

$R^{1B}$ and $R^{1C}$ each independently represent an oxygen atom or $NR^{102}$. $R^{102}$ represents a hydrogen atom or an alkyl group. The alkyl group represented by $R^{102}$ has the same definition as the alkyl group represented by $R^{101}$ in Formula (1), and the suitable embodiments thereof are also the same. As $R^{102}$, a hydrogen atom is preferable.

b and c each independently represent an integer of 1 to 5. However, b and c satisfy $2 \leq b+c \leq 6$.

In view of further improving the substrate adhesion, b+c is preferably 2 to 4, and more preferably 2 or 3. b is preferably 1 to 3, and more preferably 1. Furthermore, c is preferably 1 to 3, and more preferably 1.

$L^3$ represents a (b+1)-valent aliphatic hydrocarbon group which contains a urethane bond (—NH—CO—O— or —O—CO—NH—) or a urea bond (—NH—CO—NH—) and may contain —O—. That is, $L^3$ is linked to b pieces of monovalent group represented by Formula (Y) and a nitrogen atom (cationized nitrogen atom) specified in Formula (1).

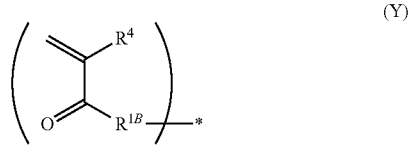

(Y)

In Formula (Y), $R^4$ and $R^{1B}$ have the same definitions as $R^4$ and $R^{1B}$ in Formula (2). * represents a position linked to $L^3$.

The number of carbon atoms in the aliphatic hydrocarbon group represented by $L^3$ is not particularly limited, but is, for example, 1 to 30, preferably 1 to 20, more preferably 1 to 15, and even more preferably 1 to 12.

Furthermore, the aliphatic hydrocarbon group may have a substituent. The substituent that the aliphatic hydrocarbon group can have is not particularly limited, and examples thereof include a substituent W which will be described later.

In $L^3$, a carbon atom is usually located at a position adjacent to a nitrogen atom (cationized nitrogen atom) specified in the chemical formula and at a position adjacent to $R^{1B}$.

Examples of $L^3$ include a linking group represented by Formula (2A-1), a linking group represented by Formula (2A-2), and a linking group represented by Formula (2A-3).

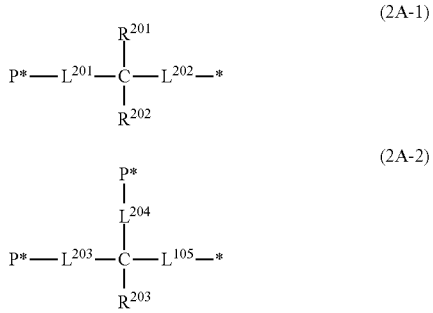

(2A-1)

(2A-2)

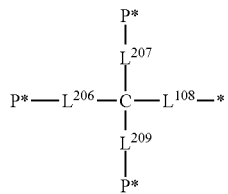

(2A-3)

In Formulas (2A-1) and (2A-2), $R^{201}$ to $R^{203}$ each represent a hydrogen atom or a substituent. The substituent is not particularly limited, and examples thereof include the substituent W which will be described later.

In the formulas (2A-1) to (2A-3), $L^{201}$ to $L^{209}$ each represent a single bond or an alkylene group which may contain —O—, a urethane bond, or a urea bond. However, in Formula (2A-1), any one or more groups between $L^{201}$ and $L^{202}$ represent an alkylene group which contains a urethane bond or a urea bond and may contain —O—. In Formula (2A-2), any one or more groups among $L^{203}$ to $L^{205}$ represent an alkylene group which contains a urethane bond or a urea bond and may contain —O—. In Formula (2A-3), any one or more groups among $L^{206}$ to $L^{209}$ represent an alkylene group which contains a urethane bond or a urea bond and may contain —O—.

The number of carbon atoms in the alkylene group, which is represented by $L^{201}$ to $L^{209}$ and may contain —O—, a urethane bond, or a urea bond, is not particularly limited, but is preferably 1 to 12, more preferably 1 to 6, and even more preferably 1 to 3. In addition, the alkylene group which is represented by $L^{201}$ to $L^{209}$ and may contain —O—, a urethane bond, or a urea bond may be linear, branched, or cyclic.

P* represents a position linked to the monovalent group represented by Formula (Y), and * represents a position linked to a nitrogen atom (cationized nitrogen atom) specified in Formula (2).

$L^{201}$ to $L^{209}$ may further have a substituent. The substituent is not particularly limited, and examples thereof include the substituent W which will be described later. In $L^{201}$ to $L^{209}$, a carbon atom is usually located at a position linked to P* or a position linked to a nitrogen atom (cationized nitrogen atom) specified in Formula (2).

$L^4$ represents a (c+1)-valent aliphatic hydrocarbon group which contains a urethane bond (—NH—CO—O— or —O—CO—NH—) or a urea bond (—NH—CO—NH—) and may contain —O—. That is, $L^4$ is linked to c pieces of monovalent group represented by Formula (Z) and a nitrogen atom (cationized nitrogen atom) specified in Formula (2).

(Z)

In Formula (Z), $R^6$ and $R^{1C}$ have the same definitions as $R^6$ and $R^{1C}$ in Formula (2). * represents a position linked to $L^4$.

The number of carbon atoms in the aliphatic hydrocarbon group represented by $L^4$ is not particularly limited, but is, for example, 1 to 30, preferably 1 to 20, more preferably 1 to 15, and even more preferably 1 to 12.

Furthermore, the aliphatic hydrocarbon group may have a substituent. The substituent that the aliphatic hydrocarbon group can have is not particularly limited, and examples thereof include a substituent W which will be described later.

In $L^4$, a carbon atom is usually located at a position adjacent to a nitrogen atom (cationized nitrogen atom) specified in the chemical formula and at a position adjacent to $R^{1C}$.

Examples of $L^4$ include a linking group represented by Formula (3A-1), a linking group represented by Formula (3A-2), and a linking group represented by Formula (3A-3).

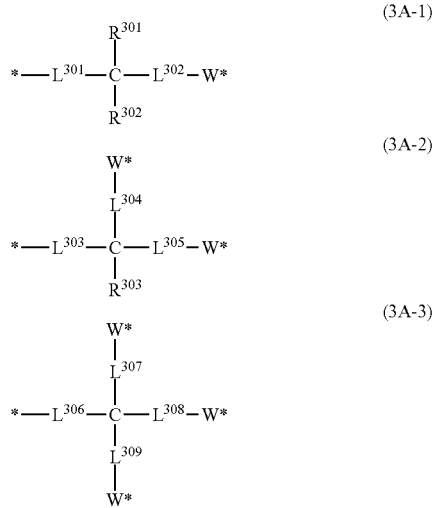

In Formulas (3A-1) and (3A-2), $R^{301}$ to $R^{303}$ each represent a hydrogen atom or a substituent. The substituent is not particularly limited, and examples thereof include the substituent W which will be described later.

In the formulas (3A-1) to (3A-3), $L^{301}$ to $L^{309}$ each represent a single bond or an alkylene group which may contain —O—, a urethane bond, or a urea bond. However, in Formula (3A-1), any one or more groups between $L^{301}$ and $L^{302}$ represent an alkylene group which contains a urethane bond or a urea bond and may contain —O—. In Formula (3A-2), any one or more groups among $L^{303}$ to $L^{305}$ represent an alkylene group which contains a urethane bond or a urea bond and may contain —O—. In Formula (3A-3), any one or more groups among $L^{306}$ to $L^{309}$ represent an alkylene group which contains a urethane bond or a urea bond and may contain —O—.

The number of carbon atoms in the alkylene group, which is represented by $L^{301}$ to $L^{309}$ and may contain —O—, a urethane bond, or a urea bond, is not particularly limited, but is preferably 1 to 12, more preferably 1 to 6, and even more preferably 1 to 3. In addition, the alkylene group which is represented by $L^{301}$ to $L^{309}$ and may contain —O—, a urethane bond, or a urea bond may be linear, branched, or cyclic.

W* represents a position linked to the monovalent group represented by Formula (Z), and * represents a position linked to a nitrogen atom (cationized nitrogen atom) specified in Formula (2).

$L^{301}$ to $L^{309}$ may further have a substituent. The substituent is not particularly limited, and examples thereof include the substituent W which will be described later. In $L^{301}$ to $L^{309}$, a carbon atom is usually located at a position linked to W* or at a position linked to the nitrogen atom (cationized nitrogen atom) specified in Formula (2).

In Formula (2), the total number of P* in $L^3$ and W* in $L^4$ is 2 to 6.

$L^5$ represents an alkylene group which may contain —O—, —$NR^{204}$—, —CO—, or a divalent linking group obtained by combining these.

$R^{204}$ represents a hydrogen atom or a substituent. The substituent represented by $R^{204}$ is not particularly limited, and examples thereof include the substituent W which will be described later. Among these, a hydrogen atom is preferable as $R^{204}$.

$L^5$ has the same definition as $L^2$ in Formula (1), and the suitable embodiments thereof are also the same.

$A^2$ represents S=O or a carbon atom. In view of further improving the biocompatibility, $A^2$ is preferably S=O.

The specific betaine monomer can be synthesized according to a known method.

One kind of the specific betaine monomer may be used singly, or two or more kinds of the specific betaine monomers may be used in combination.

In the composition according to the embodiment of the present invention, the content of the betaine monomer (total content in a case where the composition contains a plurality of kinds of the betaine monomers) with respect to the total solid content of the composition is preferably 10% to 99% by mass, more preferably 20% to 85% by mass, and even more preferably 50% to 85% by mass.

In the present specification, "solid content" means components constituting a cured product and does not include a solvent. A monomer is a component constituting the cured product. Therefore, the monomer is included in the solid content even if the monomer is a liquid.

Specific examples of the specific betaine monomer will be shown below, but the present invention is not limited thereto.

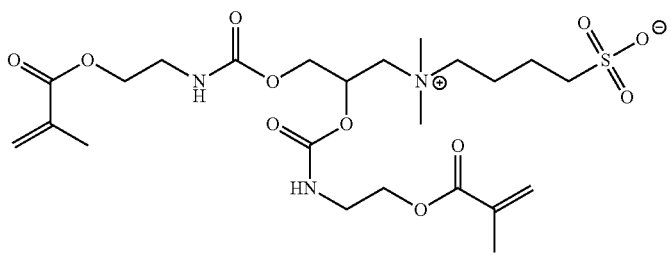

-continued
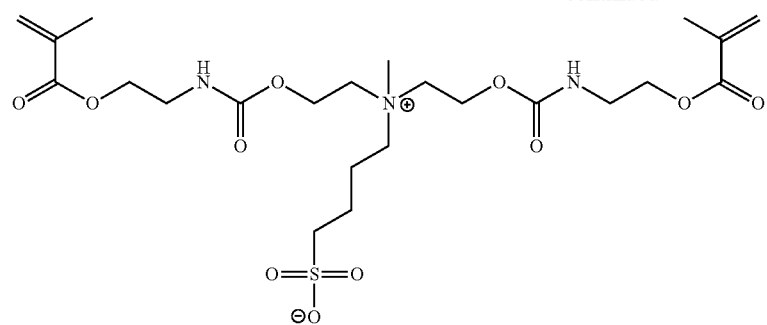
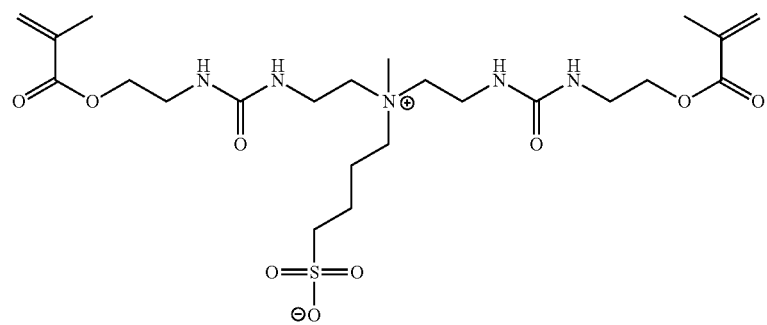
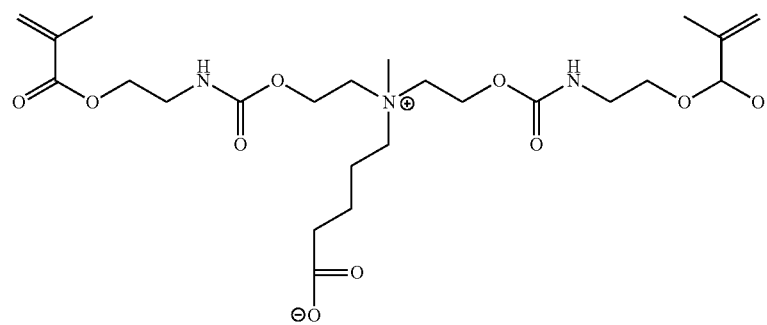
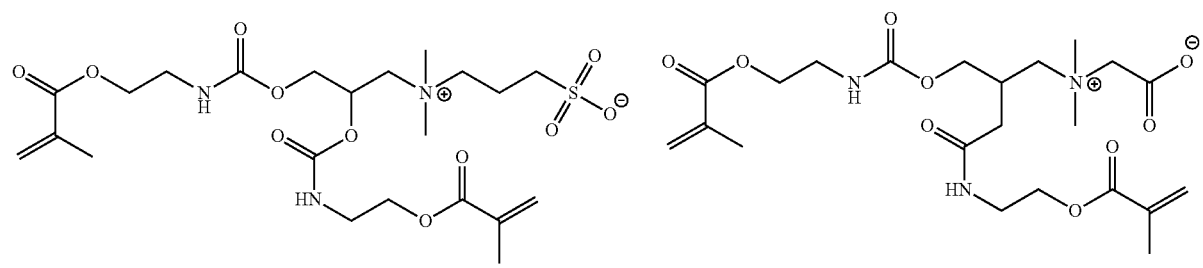
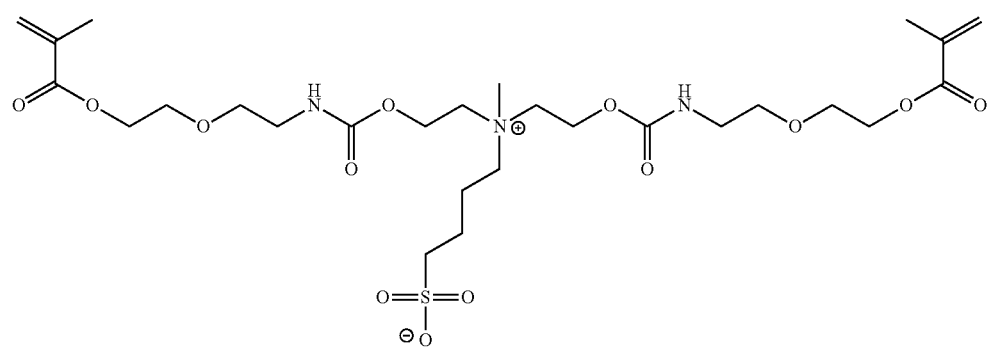

[Copolymerizable Monomer]

In view of further improving the substrate adhesion, the composition according to the embodiment of the present invention may contain a monomer copolymerizable with the specific betaine monomer (hereinafter, simply referred to as "copolymerizable monomer" as well).

The copolymerizable monomer is not particularly limited, and examples thereof include a monomer having an ethylenically unsaturated group. Examples of the monomer include (meth)acrylate-based monomers; (meth)acrylamide-based monomers; monomers having an ethylenically unsaturated group containing a carboxyl group (carboxylic acid group-containing monomers), such as (meth)acrylic acid, crotonic acid, and itaconic acid; and monomers having a betaine structure. The number of ethylenically unsaturated bonds in a molecule of the monomer having an ethylenically unsaturated group is not particularly limited, but is preferably 1 to 8, more preferably 1 to 4, and even more preferably 1 or 2.

As the copolymerizable monomer, a (meth)acrylate-based monomer, a (meth)acrylamide-based monomer, or a monomer having a betaine structure other than the specific betaine monomer is preferable.

<(Meth)Acrylate-Based Monomer>

Examples of the (meth)acrylate-based monomer include methyl (meth)acrylate, ethyl (meth)acrylate, n-butyl (meth)acrylate, 2-ethylhexyl (meth)acrylate, 2-methoxyethyl (meth)acrylate, 2-hydroxyethyl (meth)acrylate, 2-hydroxy-1,3-propylenediol diacrylate, 2-hydroxypropyl (meth)acrylate, 3-(meth)acryloyloxypropyl sulfonate, N,N-dimethylaminoethyl (meth)acrylate, N,N-diethylaminoethyl (meth)acrylate, polyalkylene glycol mono(meth)acrylate, polyalkylene glycol di(meth)acrylate, 2-(meth)acryloyloxyethyl methyl sulfoxide, tetraethylene glycol dimethacrylate, urethane dimethacrylate, trimethylolpropane tri(meth)acrylate, and the like.

<(Meth)Acrylamide-Based Monomer>

Examples of the (meth)acrylamide-based monomer include (meth)acrylamide, N-methyl (meth)acrylamide, N-2-hydroxyethyl (meth)acrylamide, a polyfunctional (meth)acrylamide compound represented by Formula (A), and the like.

Hereinafter, the polyfunctional (meth)acrylamide compound represented by Formula (A) will be described.

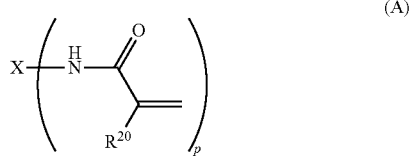

(A)

In the formula, $R^{20}$ represents a hydrogen atom or a methyl group. A plurality of $R^{20}$s may be the same as or different from each other.

X represents a p-valent linking group. p represents an integer of 2 to 4.

X is not particularly limited, and examples thereof include an alkylene group which may contain one or more kinds of divalent linking groups selected from the group consisting of —O—, —S—, —NR$^A$—, —CO—, and Formula (B) and a group represented by Formula (T$^1$), and a group represented by Formula (T2). The number of carbon atoms in the alkylene group is not particularly limited, but is, for example, 1 to 100. $R^A$ represents a hydrogen atom or an alkyl group (for example, the alkyl group has 1 to 6 carbon atoms and preferably has 1 to 3 carbon atoms).

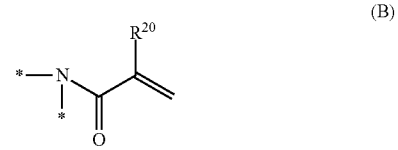

(B)

In Formula (B), $R^{20}$ represents a hydrogen atom or a methyl group. In addition, * represents a linking position.

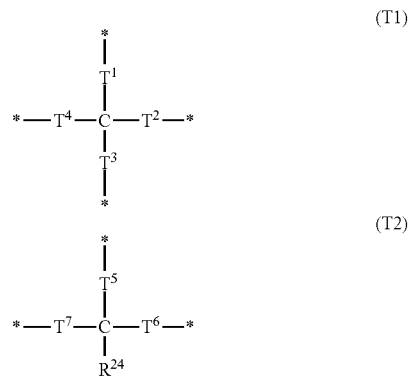

In the formulas (T$^1$) and (T2), T$^1$ to T$^7$ each independently represent a single bond or a divalent linking group. The divalent linking group is not particularly limited, and examples thereof include an alkylene group having 1 to 10 carbon atoms that may contain one or more divalent linking groups selected from the group consisting of —O—, —S—, —NR$^A$—, and —CO—. Particularly, in view of further improving the substrate adhesion, T$^1$ to T$^7$ more preferably each independently represent an alkylene group having 2 to 4 carbon atoms containing —O—. In T$^1$ to T$^7$, it is preferable that a carbon atom is located at a position adjacent to a nitrogen atom in the amide group specified in Formula (A).

In the group represented by Formula (T2), $R^{24}$ represents a hydrogen atom or a substituent. The substituent represented by $R^{24}$ is not particularly limited, and examples thereof include the substituent W which will be described later. The substituent represented by $R^{24}$ particularly preferably an alkyl group (any of a linear, branched, or cyclic alkyl group preferably having 1 to 10 carbon atoms and more preferably having 1 to 6 carbon atoms). $R^{24}$ represents a hydrogen atom or an alkyl group (for example, the alkyl group has 1 to 6 carbon atoms and preferably has 1 to 3 carbon atoms).

In view of further improving the biocompatibility, the polyfunctional (meth)acrylamide compound represented by Formula (A) is preferably a compound represented by Formula (A1) or a compound represented by Formula (A2).

(Compound Represented by Formula (A1))

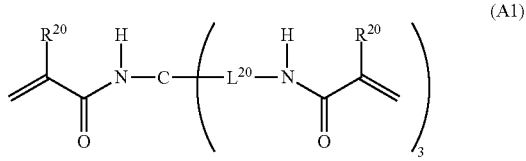

In Formula (A1), $R^{20}$ each independently represents a hydrogen atom or a methyl group. A plurality of $R^{20}$s may be the same as or different from each other.

$L^{20}$ each independently represents —O—, an alkylene group having 2 to 4 carbon atoms, or a divalent linking group obtained by combining these. In $L^{20}$, it is preferable that a carbon atom is located at a position adjacent to a nitrogen atom in the amide group specified in the chemical formula. That is, as the group adjacent to a nitrogen atom in the amide group, an alkylene group having 2 to 4 carbon atoms is preferably located at the aforementioned position.

Examples of the aforementioned "divalent linking group obtained by combining these" include an alkylene group having 2 to 4 carbon atoms containing —O—, such as —OCH$_2$CH$_2$—, —OCH$_2$CH$_2$CH$_2$—, —OCH$_2$CH$_2$CH$_2$CH$_2$—, —CH$_2$OCH$_2$—, —CH$_2$OCH$_2$CH$_2$—, or —CH$_2$OCH$_2$CH$_2$CH$_2$— and a group represented by —(O-alkylene group (having 2 to 4 carbon atoms))$_n$-, and the like. Herein, n represents an integer of 2 or greater. The upper limit of n is not particularly limited, but is, for example, about 10.

In each of the groups exemplified as "divalent linking group obtained by combining these", any of the two binding sites may be bonded to the amide group.

Particularly, in view of further improving the substrate adhesion and the biocompatibility, $L^{20}$ is preferably an alkylene group having 2 to 4 carbon atoms containing —O—.

Furthermore, a plurality of $L^{20}$s may be the same as or different from each other.

(Compound Represented by Formula (A2))

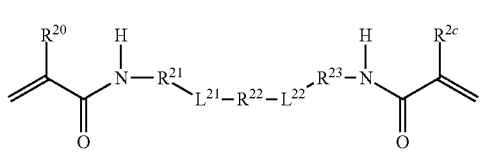

In Formula (A2), $R^{20}$ each independently represents a hydrogen atom or a methyl group.

$R^{21}$ and $R^{23}$ each independently represent —O—, an alkylene group having 1 to 4 carbon atoms, or a divalent linking group obtained by combining these. In $R^{21}$ and $R^{23}$, it is preferable that a carbon atom is usually located at a position adjacent to a nitrogen atom in the amide group specified in the chemical formula. As the group adjacent to a nitrogen atom in the amide group, an alkylene group having 1 to 4 carbon atoms is preferably located at the aforementioned position.

Examples of the "divalent linking group obtained by combining these" include an alkylene group having 1 to 4 carbon atoms containing —O—, such as —OCH$_2$—, —OCH$_2$CH$_2$—, —OCH$_2$CH$_2$CH$_2$—, —OCH$_2$CH$_2$CH$_2$CH$_2$—, —CH$_2$OCH$_2$—, —CH$_2$OCH$_2$CH$_2$—, or —CH$_2$OCH$_2$CH$_2$CH$_2$—, and a group represented by —(O-alkylene group (having 1 to 4 carbon atoms))$_n$-. Herein, n represents an integer of 2 or greater. The upper limit of n is not particularly limited, but is, for example, about 10.

In each of the groups exemplified as "divalent linking group obtained by combining these", any of the two binding sites may be bonded to the amide group.

Particularly, in view of further improving the substrate adhesion and the biocompatibility, $R^{21}$ and $R^{23}$ more preferably each independently represent an alkylene group having 1 to 4 carbon atoms or an alkylene group having 1 to 4 carbon atoms containing —O—.

In Formula (A2), $R^{22}$ represents —O—, an alkylene group having 1 to 4 carbon atoms, a group represented by Formula (B), or a divalent linking group obtained by combining these.

Examples of the "divalent linking group combining these" include the groups described above for $R^{21}$ and $R^{23}$. In a case where the group represented by Formula (B) is combined with another group, it is preferable that an alkylene group having 1 to 4 carbon atoms is bonded to a nitrogen atom in the group represented by Formula (B).

Particularly, in view of further improving the substrate adhesion and the biocompatibility, $R^{22}$ is more preferably an alkylene group having 1 to 4 carbon atoms, an alkylene group having 1 to 4 carbon atoms containing —O—, or the group represented by Formula (B).

$L^{21}$ and $L^{22}$ each independently represent a single bond or a group represented by Formula (B).

In a case where $R^{22}$ represents Formula (B), it is preferable that both the $L^{21}$ and $L^{22}$ represent a single bond.

In Formula (B), * represents a binding position.

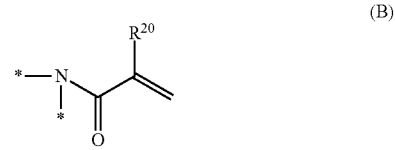

In Formula (B), $R^{20}$ represents a hydrogen atom or a methyl group, and * represents a linking position. Usually, a carbon atom is located at *.

Specific examples of the polyfunctional (meth)acrylamide compound represented by Formula (A) will be shown below, but the present invention is not limited thereto.

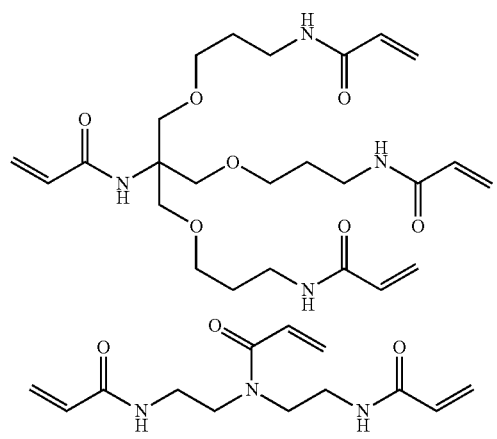

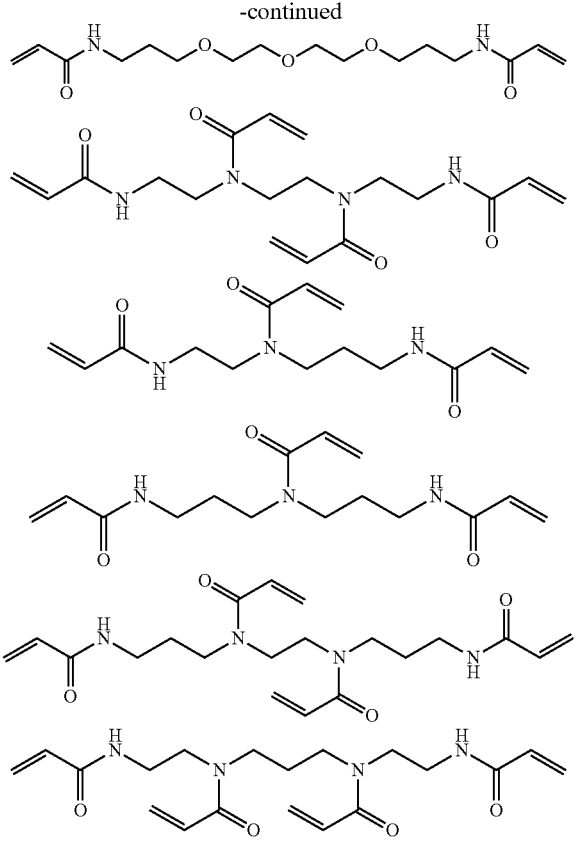

As the polyfunctional (meth)acrylamide compound represented by Formula (A), various commercially available products can be used. Alternatively, the specific polyfunctional (meth)acrylamide compound can be synthesized by the method described in Journal of Technical Disclosure No. 2013-502654.

<Betaine Monomer>

The betaine monomer other than the specific betaine monomer is not particularly limited, and examples thereof include a monomer having a betaine structure such as a sulfobetaine structure, a phosphobetaine structure, or a carboxybetaine structure. The skeleton of the betaine monomer that the composition according to the embodiment of the present invention can contain is not particularly limited, but is preferably an acrylate-based monomer or an acrylamide-based monomer is preferable. Specifically, examples of the betaine monomer include those described in WO2017/018146A and the like.

Particularly, in view of further improving the biocompatibility, as the betaine monomer, a compound represented by Formula (C) is preferable.

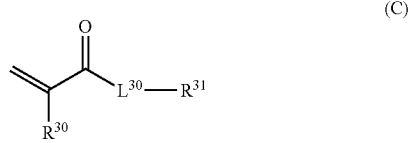

In Formula (C), $R^{30}$ represents a hydrogen atom or an alkyl group.

The alkyl group represented by $R^{30}$ has the same definition as the alkyl group represented by $R^1$ in Formula (1) described above, and the suitable embodiments thereof are also the same. As $R^{30}$, particularly, a hydrogen atom or an alkyl group having 1 to 6 carbon atoms is preferable, and a hydrogen atom or an alkyl group having 1 to 3 carbon atoms is more preferable.

$L^{30}$ represents an oxygen atom or —$NR^4$—.

$R^4$ represents a hydrogen atom or an alkyl group. The alkyl group represented by $R^4$ has the same definition as the alkyl group represented by $R^{101}$ in Formula (1) described above, and the suitable embodiments thereof are also the same. As $R^4$, a hydrogen atom is particularly preferable.

$R^{31}$ represents a monovalent group represented by Formula (I), a monovalent group represented by Formula (II), or a monovalent group represented by Formula (III).

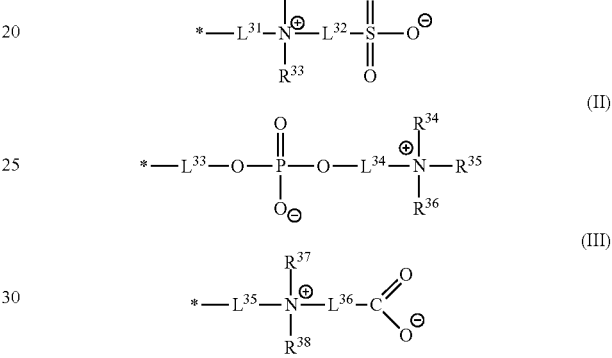

In Formula (I), $L^{31}$ and $L^{32}$ each independently represent a divalent linking group.

$L^{31}$ and $L^{32}$ are not particularly limited, but may be an alkylene group having 1 to 10 carbon atoms that may contain a heteroatom (the alkylene group may be any of a linear, branched, or cyclic alkylene group, but is preferably a linear alkylene group). The number of carbon atoms in the alkylene group is more preferably 1 to 6, even more preferably 1 to 4, and particularly preferably 2 to 4.

$R^{32}$ and $R^{33}$ each independently represent an alkyl group.

The number of carbon atoms in the alkyl group represented by $R^{32}$ and $R^{33}$ is not particularly limited, but is preferably 1 to 6 and more preferably 1 to 3. The alkyl group may be linear, branched, or cyclic.

Examples of the alkyl group include a methyl group, an ethyl group, a n-propyl group, and an isopropyl group.

The alkyl group may have a substituent. The substituent that the alkyl group can have is not particularly limited, and examples thereof include a substituent W which will be described later.

* represents a binding position.

In Formula (II), $L^{33}$ and $L^{34}$ each independently represent a divalent linking group.

The divalent linking group represented by $L^{33}$ and $L^{34}$ has the same definition as the divalent linking group represented by $L^{31}$ and $L^{32}$ in Formula (I) described above, and the suitable embodiments thereof are also the same.

$R^{34}$ to $R^{36}$ each independently represent an alkyl group.

The alkyl group represented by $R^{34}$ to $R^{36}$ has the same definition as the alkyl group represented by $R^{32}$ and $R^{33}$ in Formula (I) described above, and the suitable embodiments thereof are also the same.

* represents a binding position.

In Formula (III), $L^{35}$ and $L^{36}$ each independently represent a divalent linking group.

The divalent linking group represented by $L^{35}$ and $L^{36}$ has the same definition as the divalent linking group represented by $L^{31}$ and $L^{32}$ in Formula (I) described above, and the suitable embodiments thereof are also the same.

$R^{37}$ and $R^{38}$ each independently represent an alkyl group.

The alkyl group represented by $R^{37}$ and $R^{38}$ has the same definition as the alkyl group represented by $R^{32}$ and $R^{33}$ in Formula (I) described above, and the suitable embodiments thereof are also the same.

\* represents a binding position.

Particularly, in view of further improving the biocompatibility, as $R^{31}$, the group represented by Formula (I) or the group represented by Formula (II) is preferable.

The betaine monomer can be synthesized by a known method.

Specific examples of the betaine monomer will be shown below, but the present invention is not limited thereto.

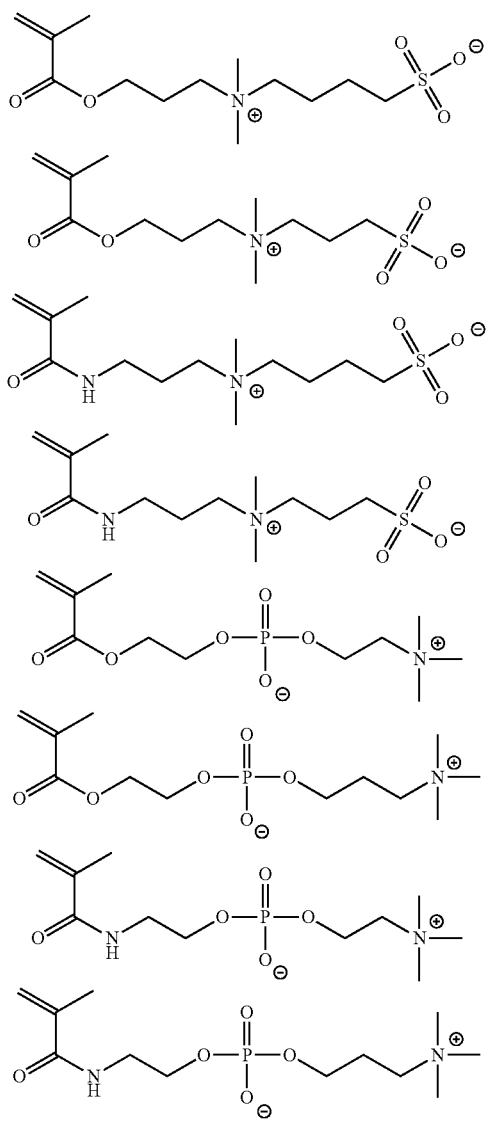

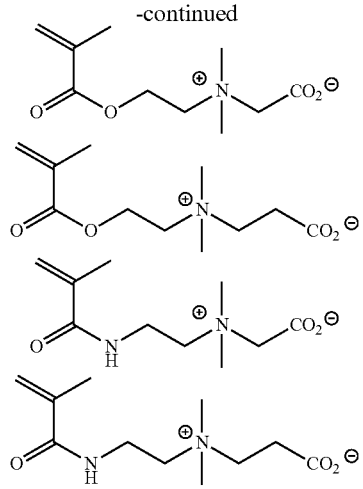

One kind of the copolymerizable monomer may be used singly, or two or more kinds of the copolymerizable monomers may be used in combination.

In the composition according to the embodiment of the present invention, the content of the copolymerizable monomer (total content in a case where the composition contains a plurality of kinds of the copolymerizable monomers) with respect to the total solid content of the composition is preferably 0% to 60% by mass, more preferably 10% to 50% by mass, and even more preferably cop to 40% by mass. In a case where the copolymerizable monomer is a betaine monomer, in the composition according to the embodiment of the present invention, the content of the betaine monomer (total content in a case where the composition contains a plurality of kinds of the betaine monomers) with respect to the total solid content of the composition is preferably 0% to 30% by mass, and more preferably 10% to 25% by mass.

(Substituent Group W)

Examples of the substituent W includes an alkyl group (preferably an alkyl group having 1 to 20 carbon atoms), an alkenyl group (preferably an alkenyl group having 2 to 20 carbon atoms), an alkynyl group (preferably an alkynyl group having 2 to 20 carbon atoms), a cycloalkyl group (preferably a cycloalkyl group having 3 to 20 carbon atoms), an aryl group (preferably an aryl group having 6 to 26 carbon atoms), a heterocyclic group (preferably a heterocyclic group having 2 to 20 carbon atoms and more preferably a 5- or 6-membered heterocyclic group having at least one oxygen atom, sulfur atom, or nitrogen atom), an alkoxy group (preferably an alkoxy group having 1 to 20 carbon atoms), an aryloxy group (preferably an aryloxy group having 6 to 26 carbon atoms), an alkoxycarbonyl group (preferably an alkoxycarbonyl group having 2 to 20 carbon atoms), an aryloxycarbonyl group (preferably an aryloxycarbonyl group having 6 to 26 carbon atoms), an amino group (preferably an amino group having 0 to 20 carbon atoms including an alkylamino group and an arylamino group, such as amino, N,N-dimethylamino, N,N-diethylamino, N-ethylamino, and anilino), a sulfamoyl group (preferably a sulfamoyl group having 0 to 20 carbon atoms), an acyl group (preferably an acyl group having 1 to 20 carbon atoms), an acyloxy group (preferably an acyloxy group having 1 to 20 carbon atoms), a carbamoyl group (preferably a carbamoyl group having 1 to 20 carbon atoms), an acylamino group (preferably an acylamino group having 1 to 20 carbon atoms, such as an acetylamino group or a benzoylamino group), an alkylthio group (preferably an alkylthio group having 1 to 20 carbon atoms), an arylthio group (preferably an arylthio group having 6 to 26 carbon atoms), an alkylsulfonyl group (preferably an alkylsulfonyl group having 1 to 20 carbon atoms), an arylsulfonyl group (preferably an arylsulfonyl group having 6 to 22 carbon atoms), an alkylsilyl group (preferably an alkylsilyl group having 1 to 20 carbon atoms), an arylsilyl group (preferably an arylsilyl group having 6 to 42 carbon atoms), an alkoxysilyl group (preferably an alkoxysilyl group having 1 to 20 carbon atoms), an aryloxysilyl group (preferably an aryloxysilyl group having 6 to 42 carbon atoms), a phosphoryl group (preferably a phosphoryl group having 0 to 20 carbon atoms, for example, —OP(=O)($R^P$)$_2$), a phosphonyl group (preferably a phosphonyl group having 0 to 20 carbon atoms, for example, —P(=O)($R^P$)$_2$), a phosphinyl group (preferably a phosphinyl group having 0 to 20 carbon atoms, for example, —P($R^P$)$_2$), a (meth)acryloyl group, a (meth)acryloyloxy group, a (meth)acryloylimino group (a (meth)acrylamide group), a hydroxyl group, a thiol group, a carboxyl group, a phosphoric acid group, a phosphonic acid group, a sulfonic acid group, a cyano group, and a halogen atom (for example, a fluorine atom, a chlorine atom, a bromine atom, an iodine atom, or the like). $R^P$ represents a hydrogen atom, a hydroxyl group, or a substituent.

In addition, each of the groups exemplified as the substituent W may be further substituted with the substituent W.

In a case where the aforementioned substituent is an acidic group or a basic group, the substituent may form a salt thereof.

In a case where the compound, the substituent, the linking group, and the like contain an alkyl group, an alkylene group, an alkenyl group, an alkenylene group, an alkynyl group, an alkynylene group, or the like, these may be cyclic or chainlike or may be linear or branched, and may be substituted as described above or unsubstituted.

[Initiator]

It is preferable that the composition according to the embodiment of the present invention contains an initiator.

The initiator is not particularly limited, but is preferably a thermal polymerization initiator or a photopolymerization initiator.

Examples of the photopolymerization initiator include an alkylphenone-based photopolymerization initiator, a methoxyketone-based photopolymerization initiator, an acylphosphine oxide-based photopolymerization initiator, a hydroxyketone-based photopolymerization initiator (for example, IRGACURE184; 1,2-α-hydroxyalkylphenone), an aminoketone-based photopolymerization initiator (for example, 2-methyl-1-[4-(methylthio)phenyl]-2-morpholinopropan-1-one (IRGACURE (registered trademark) 907)), an oxime-based photopolymerization initiator, and an oxyphenylacetic acid ester-based photopolymerization initiator (IRGACURE (registered trademark) 754), and the like.

Examples of other initiators include an azo-based polymerization initiator (for example, V-50 or V-601), a persulfate-based polymerization initiator, a persulfuric acid-based polymerization initiator, a redox-based polymerization initiator, and the like.

One kind of the initiator may be used singly, or two or more kinds of the initiators may be used in combination.

In the composition according to the embodiment of the present invention, the content of the initiator (total content in a case where the composition contains a plurality of kinds of initiators) is not particularly limited. However, the content of the initiator with respect to the total solid content of the composition is preferably 0.5% to 10% by mass, and more preferably 1% to 5% by mass.

[Solvent]

It is preferable that the composition according to the embodiment of the present invention contains a solvent.

Examples of the solvent include water, an organic solvent (for example, esters such as ethyl acetate and n-butyl acetate; aromatic hydrocarbons such as toluene and benzene; aliphatic hydrocarbons such as n-hexane and n-heptane; alicyclic hydrocarbons such as cyclohexane and methylcyclohexane; ketones such as methyl ethyl ketone (MEK), methyl isobutyl ketone, and cyclohexanone; alcohols such as methanol and butanol, or the like), and a mixed solvent of these.

Among these, from the viewpoint of making it difficult for surface unevenness to occur during coating, alcohol solvents such as methanol and ethanol are preferable.

One kind of the solvent may be used singly, or two or more kinds of the solvents may be used in combination.

In the composition according to the embodiment of the present invention, the content of the solvent (total content in a case where the composition contains a plurality of kinds of solvents) with respect to the total mass of the composition is preferably from 0.5% to 95% by mass, more preferably 1% to 90% by mass, and even more preferably 10% to 80% by mass.

[Other Components]

The composition according to the embodiment of the present invention may contain components other than the components described above. Examples of such components include a binder resin, a polyfunctional amine, a polyfunctional thiol, a surfactant, a plasticizer, and a surface lubricant, a leveling agent, a softener, an antioxidant, an antiaging agent, a light stabilizer, an ultraviolet absorber, an inorganic or organic filler, a metal powder, and the like.

The binder resin is not particularly limited, and examples thereof include an acrylic resin, a styrene-based resin, a vinyl-based resin, a polyolefin-based resin, a polyester-based resin, a polyurethane-based resin, a polyamide-based resin, a polycarbonate-based resin, a polydiene-based resin, an epoxy-based resin, a silicone-based resin, a cellulose-based polymer, a chitosan-based polymer, and the like.

[Method for Preparing Curable Composition]

As the method for preparing the composition according to the embodiment of the present invention, a known method can be employed without particular limitation. For example, the curable composition can be prepared by mixing together the above components and then stirring the mixture by known means.

[Cured Product]

The cured product according to an embodiment of the present invention is formed by curing the aforementioned composition according to the embodiment of the present invention.

The shape of the cured product can be appropriately selected according to the use. Examples of the shape of the cured product include a powder shape and a film shape. Among these, a film shape is preferable.

In a case where the cured product is formed into a film, the film thickness is not particularly limited, but is, for example, 0.1 to 300 μm and more preferably 1 to 100 inm.

The cured product according to the embodiment of the present invention contains a polymer compound containing a repeating unit derived from the specific betaine monomer described above.

[Method for Manufacturing Cured Product (Cured Film)]

The method for manufacturing the cured product (cured film) according to the embodiment of the present invention is not particularly limited. Examples thereof include a method of coating a substrate with the aforementioned composition according to the embodiment of the present invention and then curing the composition by heating or light irradiation (examples of the light include ultraviolet rays, visible rays, X-rays, and the like).

The material of the substrate is not particularly limited, and examples thereof include a metal material, a ceramic material, a plastic material, and the like.

Examples of the type of the plastic material include polyethylene terephthalate, polybutylene terephthalate, polyethylene naphthalate, polyethylene, polypropylene, cellophane, diacetyl cellulose, triacetyl cellulose, acetyl cellulose butyrate, polyvinyl chloride, polyvinylidene chloride, polyvinyl alcohol, an ethylene-vinyl acetate copolymer, polystyrene, polycarbonate, polymethylpentene, polysulfone, polyether ether ketone, polyether sulfone, polyether imide, polyimide, a fluororesin, nylon, an acrylic resin, polyamide, cycloolefin, polyether sulfan, and the like.

Examples of the type of the metal material include gold, stainless steel, a cobalt-chromium alloy, an amalgam alloy, a silver-palladium alloy, a gold-silver-palladium alloy, titanium, a nickel-titanium alloy, platinum, and the like.

Examples of the type of the ceramic material include hydroxyapatite and the like.

The shape of the substrate is not particularly limited, and may be a plate shape or a three-dimensional shape.

The method for coating the substrate with the composition according to the embodiment of the present invention is not particularly limited, and examples thereof include methods such as dipping, roll coating, kiss roll coating, gravure coating, reverse coating, roll brush coating, spray coating, dip roll coating, bar coating, spin coating, knife coating, air knife coating, curtain coating, lip coating, and an extrusion coating method using a die coater.

The heating method is not particularly limited, and examples thereof include a method using a blast dryer, an oven, an infrared dryer, a heating drum, and the like.

The heating temperature is not particularly limited, but is preferably 30° C. to 150° C. and more preferably 40° C. to 120° C.

The heating time is not particularly limited, but is usually 1 minute to 6 hours. In a case where the composition is dried in a coating apparatus, the heating time is 1 to 20 minutes, and the heating temperature at the time of heating after the coating (for example, heating the substrate that is wound up) is preferably room temperature to 50° C.

Examples of the method of light irradiation include methods using a low-pressure mercury lamp, a medium-pressure mercury lamp, a high-pressure mercury lamp, a metal halide lamp, a deep-UV (ultraviolet) light, an LED (light emitting diode) lamp, a xenon lamp, a chemical lamp, a carbon arc lamp, and the like. The energy of light irradiation is not particularly limited, but is preferably 0.1 to 10 $J/cm^2$.

<Use>

The cured product according to the embodiment of the present invention exhibits excellent substrate adhesion and can inhibit or prevent the adhesion of biological materials such as cells and blood components. The cured product according to the embodiment of the present invention can be suitably used for prostheses, medical instruments, and the like as a material applied to a living body (biomaterial). Specifically, the cured product according to the embodiment of the present invention may be used as a filler for a resin composition used as a material for a prosthesis, a medical instrument, and the like, or may be used as a coating material by being disposed on the surface of a prosthesis or a medical instrument. Examples of the medical instrument include a denture, an artificial dialysis membrane, a catheter, and the like. The prosthesis refers to a member that is incorporated into the human body for a long-term treatment or the like, and examples thereof include an artificial blood vessel, a stent, an artificial organ, an artificial bone, an artificial valve, cultured skin, and the like.

The cured product according to the embodiment of the present invention is particularly preferably used as a dental material or an artificial bone adhesive.

[Medical Member]

The medical member according to an embodiment of the present invention includes a substrate and a cured product disposed on the substrate.

The substrate means the aforementioned prosthesis, medical instrument, and the like, and examples thereof include those made of the metal material, the ceramic material, and the plastic material described above. Specifically, examples of the substrate include dentures and artificial bones.

The cured film corresponds, for example, to the aforementioned cured product having a film shape.

EXAMPLES

Hereinafter, the present invention will be more specifically described based on examples. The materials, the amount and ratio thereof used, how to treat the materials, the treatment procedure, and the like described in the following examples can be appropriately changed as long as the gist of the present invention is maintained. Therefore, the scope of the present invention is not limited to the following examples.

[Preparation of Curable Composition]

[Various Components]

<Specific Betaine Monomer>

The specific betaine monomers (ex (1) to ex (4)) shown in Table 1 will be shown below.

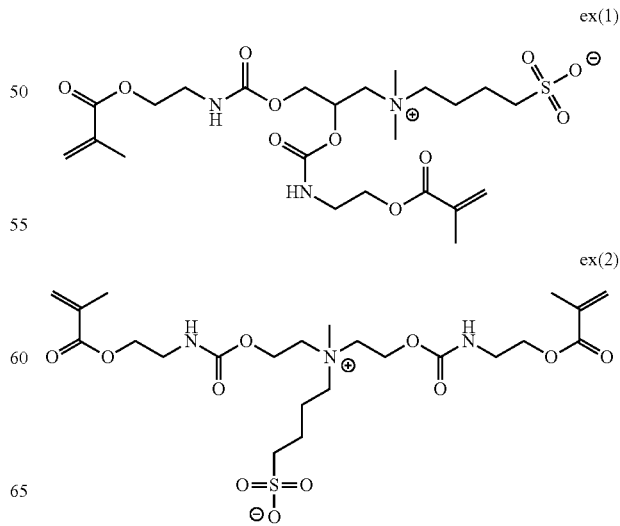

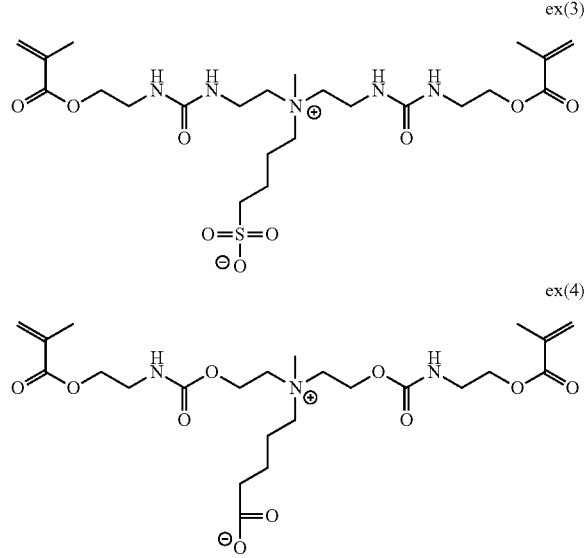

(Synthesis of Ex (1))

Hereinafter, a method for synthesizing the specific betaine monomer will be explained by describing the method for synthesizing ex (1) for example.

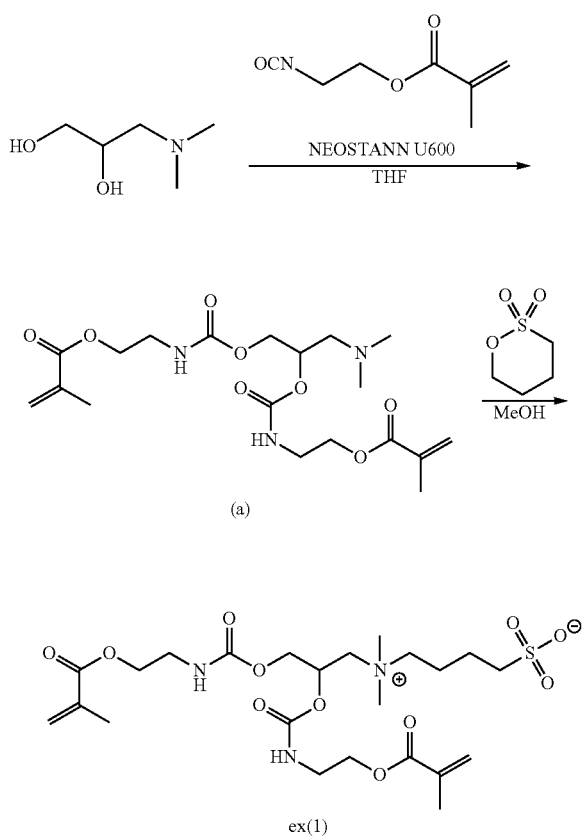

3-(Dimethylamino)-1,2-propanediol (10 g, 83.9 mmol) and tetrahydrofuran (THF, 50 mL) were mixed together, and a solution which was obtained by diluting 2-isocyanatoethyl methacrylate (27.34 g, 176 mmol) with tetrahydrofuran (50 mL) was added dropwise to the mixture. Furthermore, a solution obtained by diluting "NEOSTANN U600" (manufactured by NITTO KASEI CO., LTD., 538 mg) with tetrahydrofuran (10 mL) was added dropwise to the above solution while paying attention to heat generation, and the mixture was stirred at room temperature for 12 hours. The reaction solution was concentrated under reduced pressure, and the obtained crude product was purified by silica gel column chromatography (eluent: ethyl acetate to ethyl acetate:methanol=4:1), thereby obtaining an intermediate a (30 g, yield 83%).

The intermediate a (5 g, 11.6 mmol), 1,4-butanesultone (1.9 g, 14.0 mmol), 4-hydroxy-2,2,6,6-tetramethylpiperidine 1-oxyl free radical (60 mg, 0.35 mmol), and methanol (6 mL) were mixed together and stirred at 80° C. for 48 hours. The reaction solution was cooled to room temperature and concentrated under reduced pressure. The obtained crude product was purified by silica gel column chromatography (eluent: acetone to acetone:methanol=1:1 to methanol), thereby obtaining ex (1) (5 g, yield 76%). Through $^1$H NMR (Nuclear Magnetic Resonance), it was confirmed that the obtained product was a target substance.

$^1$H NMR (methanol-$d_4$, 400 MHz) δ: 1.82 (2H, t), 1.93 (6H, s), 1.93-2.09 (2H, m), 2.88 (2H, t), 3.15 (6H, s), 3.34-3.44 (6H, m), 3.57-3.78 (2H, m), 4.08-4.30 (6H, m), 5.63 (2H, s), 6.12 (2H, s).

Furthermore, by ESI-MS (Electrospray Ionization-Mass Spectrometry), a peak corresponding to the molecular weight of the target substance was confirmed.

(Synthesis of ex (2) to ex (4))

According to the method for synthesizing ex (1), ex (2) to ex (4) were synthesized.

(Synthesis of ex (5))

ex (5) was synthesized according to the following synthesis scheme. That is, ex (5) was synthesized by the same method as that used for synthesizing ex (1), except that for the intermediate (a), potassium chloroacetate was used instead of 1,4-butanesultone and IPA was used instead of methanol.

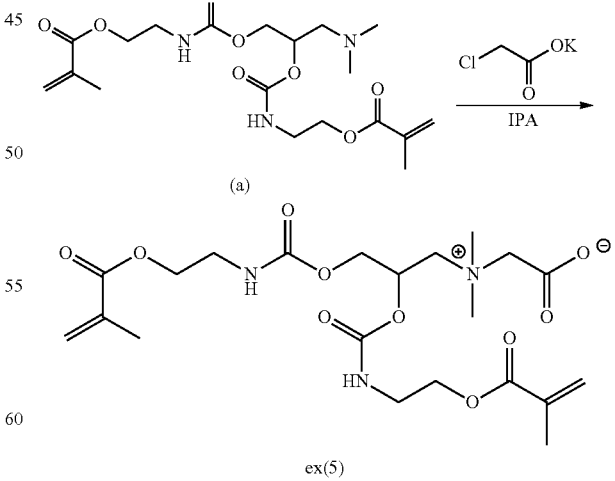

<Copolymerizable Monomer>

The copolymerizable monomers (B (1) to B (16)) shown in Table 1 will be shown below.

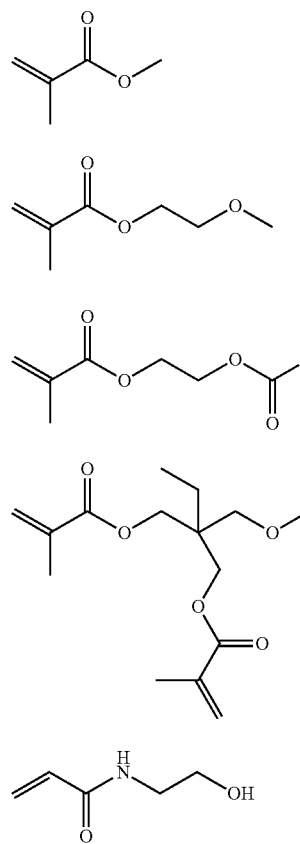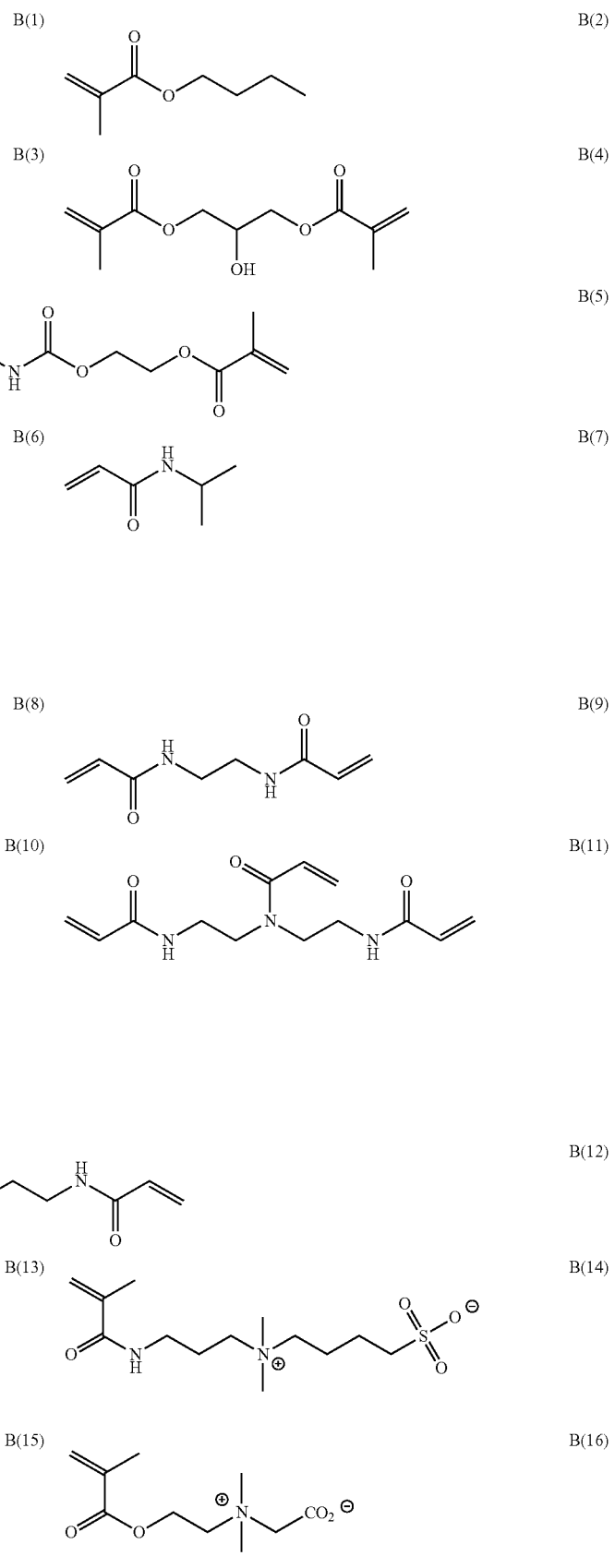

<Comparative Betaine Monomer>
Comparative betaine monomers (com (1) to com (4)) shown in Table 1 will be shown below.

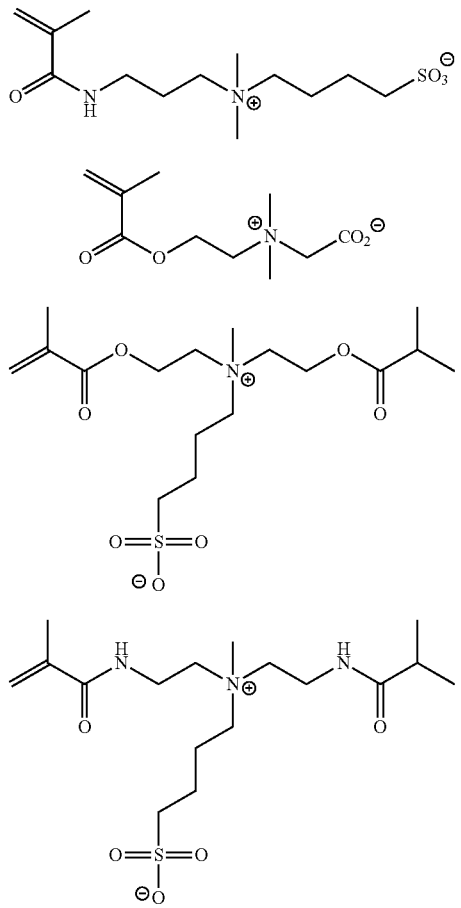

[Preparation of Curable Composition]

The components shown in the following Table 1 were dissolved in a solvent (methanol), thereby preparing curable compositions having a concentration of solid contents of 20% by mass (curable compositions 1 to 30). Regarding the curable compositions, the solid contents mean all components except for the solvent.

The numerical value in Table 1 represents the content (% by mass) of each component with respect to the total solid content of a curable composition. "Irg2959" corresponds to a polymerization initiator ("IRGACURE 2959", manufactured by BASF SE).

[Preparation of Film]
<Preparation of Coat Film for Evaluating Substrate Adhesion and Biocompatibility>

By using a spin coater, a substrate (acrylic plate (manufacturer: MISUMI Corporation, model number: ACA)) was coated with each of the prepared curable compositions such that the film thickness became about 5 m, and then the composition was dried. Then, by using an "ECS-401G (trade name)" UV (ultraviolet) exposure machine (light source: high-pressure mercury lamp) manufactured by EYE GRAPHICS Co., Ltd., the composition was exposed at an exposure amount of 4 J/cm$^2$, thereby preparing a coat film for evaluating substrate adhesion and biocompatibility.

[Evaluation]
<Substrate Adhesion Test>

The prepared acrylic plate with a coat film was immersed in a PBS (Phosphate buffered saline) solution at 37° C. for 48 hours. Thereafter, the acrylic plate with a coat film was pulled up from the solution, and the substrate adhesion was evaluated based on the area of the coat film remaining on the acrylic plate (hereinafter, referred to as "residual coat film" as well). The area of the residual coat film with respect to the area of the acrylic plate was expressed as a percentage as a coating rate, and evaluated based on the following evaluation standard. Regarding the evaluation of the substrate adhesion, samples graded "B" or higher were regarded as acceptable. The results are shown in Table 1.

(Evaluation Standard)
"A": The coating rate was equal to or higher than 90%.
"B": The coating rate was equal to or higher than 70% and less than 90%.
"C": The coating rate was equal to or higher than 50% and less than 70%.
"D": The coating rate was less than 50%.

<Evaluation of Biocompatibility (Cell Adhesion Test)>

The prepared acrylic substrate with a coat film was placed in a 6-well plate, and mouse-derived fibroblasts (3T3 cells) were dispersed in Dulbecco's modified Eagle medium at a seeding density of $1.0 \times 10^5$ cells/cm$^2$. By using an incubator, the cells were cultured for 48 hours under the condition of 37° C. and 5% carbon dioxide.

Thereafter, the acrylic substrate with the coat film was taken out observed using a phase contrast microscope (an inverted cubic research microscope, manufactured by Olympus Corporation) so as to check whether or not the cells were attached thereto. The magnification was 4×.

This operation was performed on 10 acrylic substrates with a coat film, and biocompatibility was evaluated as below based on the number of acrylic substrates with a coat film to which cells had adhered. Regarding the evaluation of the biocompatibility, samples graded "C" or higher were regarded as acceptable. For practical use, samples graded "B" or higher are preferable. The results are shown in Table 1.

In addition, "-" shown in the column of Biocompatibility in Table 1 means that the sample could not be evaluated because the film was peeled off.

(Evaluation Standard)
"S": 0 to 1
"A": 2 to 3
"B": 4 to 6
"C": 7 to 9
"D": 10 or greater

TABLE 1

| Table 1 | Curable composition No. | Component A Type | Component A Note | Component B Type | Component B note | Polymerization initiator | Substrate adhesion | Evaluation result biocompatibility |
|---|---|---|---|---|---|---|---|---|
| Example 1 | Curable composition 1 | ex (1) (97%) | Corresponding to Formula (1)sulfobetaine | — | — | Irg2959 (3%) | B | A |
| Example 2 | Curable composition 2 | ex (2) (97%) | Corresponding to Formula (2)sulfobetaine | — | — | Irg2959 (3%) | B | A |
| Example 3 | Curable composition 3 | ex (3) (97%) | Corresponding to Formula (2)sulfobetaine | — | — | Irg2959 (3%) | B | B |
| Example 4 | Curable composition 4 | ex (4) (97%) | Corresponding to Formula (2)carboxybetaine | — | — | Irg2959 (3%) | B | B |
| Example 5 | Curable composition 5 | ex (2) (67%) | Corresponding to Formula (2)sulfobetaine | B (1) (30%) | — | Irg2959 (3%) | A | B |
| Example 6 | Curable composition 6 | ex (2) (67%) | Corresponding to Formula (2)sulfobetaine | B (2) (30%) | — | Irg2959 (3%) | A | B |
| Example 7 | Curable composition 7 | ex (2) (67%) | Corresponding to Formula (2)sulfobetaine | B (3) (30%) | — | Irg2959 (3%) | A | B |
| Example 8 | Curable composition 8 | ex (2) (67%) | Corresponding to Formula (2)sulfobetaine | B (4) (30%) | — | Irg2959 (3%) | A | B |
| Example 9 | Curable composition 9 | ex (2) (67%) | Corresponding to Formula (2)sulfobetaine | B (5) (30%) | — | Irg2959 (3%) | A | B |
| Example 10 | Curable composition 10 | ex (2) (67%) | Corresponding to Formula (2)sulfobetaine | B (6) (30%) | — | Irg2959 (3%) | A | B |
| Example 11 | Curable composition 11 | ex (2) (67%) | Corresponding to Formula (2)sulfobetaine | B (7) (30%) | — | Irg2959 (3%) | A | B |
| Example 12 | Curable composition 12 | ex (2) (67%) | Corresponding to Formula (2)sulfobetaine | B (8) (30%) | — | Irg2959 (3%) | A | B |
| Example 13 | Curable composition 13 | ex (2) (67%) | Corresponding to Formula (2)sulfobetaine | B (9) (30%) | — | Irg2959 (3%) | A | B |
| Example 14 | Curable composition 14 | ex (2) (67%) | Corresponding to Formula (2)sulfobetaine | B (10) (30%) | Corresponding to Formula (A1) | Irg2959 (3%) | A | A |
| Example 15 | Curable composition 15 | ex (2) (67%) | Corresponding to Formula (2)sulfobetaine | B (11) (30%) | Corresponding to Formula (A2) | Irg2959 (3%) | A | A |
| Example 16 | Curable composition 16 | ex (2) (67%) | Corresponding to Formula (2)sulfobetaine | B (12) (30%) | Corresponding to Formula (A2) | Irg2959 (3%) | A | A |
| Example 17 | Curable composition 17 | ex (2) (67%) | Corresponding to Formula (2)sulfobetaine | B (13) (30%) | Corresponding to Formula (A2) | Irg2959 (3%) | A | A |
| Example 18 | Curable composition 18 | ex (2) (82%) | Corresponding to Formula (2)sulfobetaine | B (14) (15%) | Corresponding to Formula (I) | Irg2959 (3%) | A | S |
| Example 19 | Curable composition 19 | ex (2) (82%) | Corresponding to Formula (2)sulfobetaine | B (15) (15%) | Corresponding to Formula (II) | Irg2959 (3%) | B | S |
| Example 20 | Curable composition 20 | ex (2) (82%) | Corresponding to Formula (2)sulfobetaine | B (16) (15%) | Corresponding to Formula (III) | Irg2959 (3%) | B | A |
| Example 21 | Curable composition 30 | ex (5) (97%) | Corresponding to Formula (1)carboxybetaine | — | — | Irg2959 (3%) | B | B |
| Comparative Example 1 | Curable composition 21 | com (1) (97%) | — | — | — | Irg2959 (3%) | D | — |
| Comparative Example 2 | Curable composition 22 | com (2) (97%) | — | — | — | Irg2959 (3%) | D | — |
| Comparative Example 3 | Curable composition 23 | com (3) (97%) | — | — | — | Irg2959 (3%) | C | A |
| Comparative Example 4 | Curable composition 24 | com (4) (97%) | — | — | — | Irg2959 (3%) | C | A |
| Comparative Example 5 | Curable composition 25 | — | — | B (1) (97%) | — | Irg2959 (3%) | A | D |
| Comparative Example 6 | Curable composition 26 | — | — | B (9) (97%) | — | Irg2959 (3%) | D | — |
| Comparative Example 7 | Curable composition 27 | — | — | B (10) (97%) | Corresponding to Formula (A1) | Irg2959 (3%) | D | — |
| Comparative Example 8 | Curable composition 28 | — | — | B (15) (97%) | Corresponding to Formula (II) | Irg2959 (3%) | D | — |
| Comparative Example 9 | Curable composition 29 | com (1) (67%) | — | B (10) (30%) | Corresponding to Formula (A1) | Irg2959 (3%) | D | — |

From the results in Table 1, it was confirmed that according to the curable compositions of Examples, a cured product having excellent substrate adhesion and excellent biocompatibility was obtained.

By the comparison of Examples 1 to 4, it was confirmed that in a case where $A^1$ in the compound represented by Formula (1) and $A^2$ in the compound represented by Formula (2) each represented S=O (that is, in a case where the compounds had a sulfobetaine structure), the biocompatibility was further improved.

By the comparison of Examples 5 to 17, it was confirmed that in a case where a polyfunctional (meth)acrylamide compound, which is selected from the group consisting of the compound represented by Formula (A1) and the compound represented by Formula (A2), was used as the copolymerizable monomer, the substrate adhesion and the biocompatibility were further improved.

On the other hand, it was confirmed that the cured product obtained from the curable composition of the comparative example did not satisfy the desired requirements.

What is claimed is:

1. A curable composition comprising:
one or more betaine monomers selected from the group consisting of a compound represented by Formula (1) and a compound represented by Formula (2),

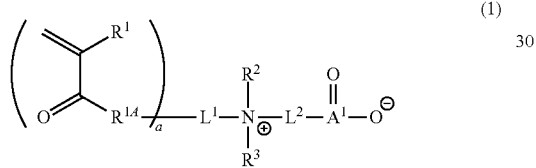

(1)

in the formula, $R^1$ represents a hydrogen atom or an alkyl group, $R^2$ and $R^3$ each independently represent an alkyl group, $R^{1A}$ represents an oxygen atom or $NR^{101}$, $R^{101}$ represents a hydrogen atom or an alkyl group, a represents an integer of 2 to 6, $L^1$ represents an (a+1)-valent aliphatic hydrocarbon group which contains a urethane bond or a urea bond and may contain —O—, $L^2$ represents an alkylene group which may contain —O—, —$NR^{104}$—, —CO—, or a divalent linking group obtained by combining these, $R^{104}$ represents a hydrogen atom or a substituent, $A^1$ represents S=O or a carbon atom,

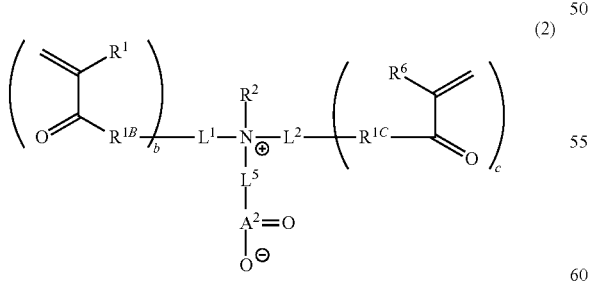

(2)

in the formula, $R^4$ and $R^6$ each independently represent a hydrogen atom or an alkyl group, $R^5$ represents an alkyl group, $R^{1B}$ and $R^{1C}$ each independently represent an oxygen atom or $NR^{102}$, $R^{102}$ represents a hydrogen atom or an alkyl group, b and c each independently represent an integer of 1 to 5, b and c satisfy 2≤b+c≤6, $L^3$ represents a (b+1)-valent aliphatic hydrocarbon group which contains a urethane bond or a urea bond and may contain —O—, $L^4$ represents a (c+1)-valent aliphatic hydrocarbon group which contains a urethane bond or a urea bond and may contain —O—, $L^5$ represents an alkylene group which may contain —O—, —$NR^{204}$—, —CO—, or a divalent linking group obtained by combining these, $R^{204}$ represents a hydrogen atom or a substituent, and $A^2$ represents S=O or a carbon atom.

2. The curable composition according to claim 1, wherein $A^1$ in Formula (1) represents S=O, and $A^2$ in Formula (2) represents S=O.

3. The curable composition according to claim 1, further comprising:
one or more monomers selected from the group consisting of a compound represented by Formula (A1) and a compound represented by Formula (A2),

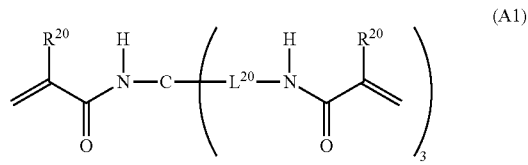

(A1)

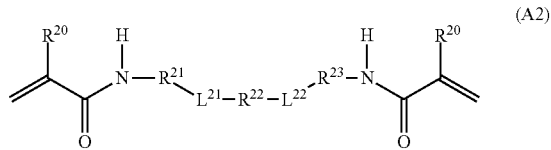

(A2)

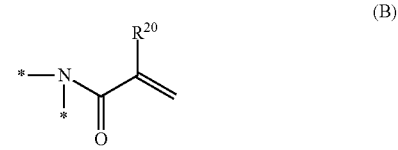

(B)

in Formula (A1), $R^{20}$ each independently represents a hydrogen atom or a methyl group, $L^{20}$ each independently represents —O—, an alkylene group having 2 to 4 carbon atoms, or a divalent linking group obtained by combining these, a plurality of $R^{20}$s may be the same as or different from each other, in Formula (A2), $R^{20}$ each independently represents a hydrogen atom or a methyl group, $R^{21}$ and $R^{23}$ each independently represent —O—, an alkylene group having 1 to 4 carbon atoms, or a divalent linking group obtained by combining these, $R^{22}$ represents —O—, an alkylene group having 1 to 4 carbon atoms, a group represented by Formula (B), or a divalent linking group obtained by combining these, $L^{21}$ and $L^{22}$ each independently represent a single bond or a group represented by Formula (B), in Formula (B), $R^{20}$ represents a hydrogen atom or a methyl group, and * represents a binding position.

4. A film comprising:
a polymer compound containing one or more repeating units selected from the group consisting of a repeating unit derived from a compound represented by Formula (1) and a repeating unit derived from a compound represented by Formula (2),

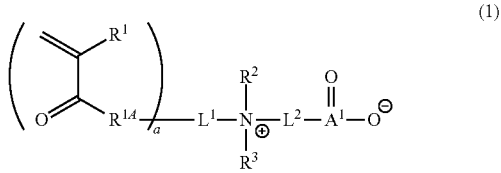

in the formula, $R^1$ represents a hydrogen atom or an alkyl group, $R^2$ and $R^3$ each independently represent an alkyl group, $R^{1A}$ represents an oxygen atom or $NR^{101}$, $R^{101}$ represents a hydrogen atom or an alkyl group, a represents an integer of 2 to 6, $L^1$ represents an (a+1)-valent aliphatic hydrocarbon group which contains a urethane bond or a urea bond and may contain —O—, $L^2$ represents an alkylene group which may contain —O—, —$NR^{104}$—, —CO—, or a divalent linking group obtained by combining these, $R^{104}$ represents a hydrogen atom or a substituent, $A^1$ represents S=O or a carbon atom,

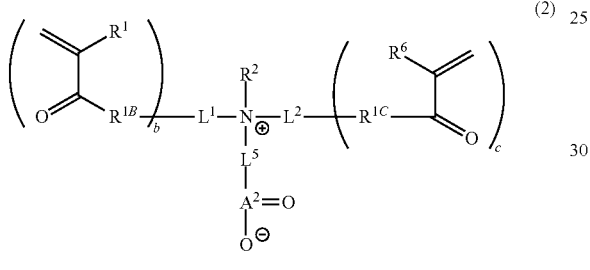

in the formula, $R^4$ and $R^6$ each independently represent a hydrogen atom or an alkyl group, $R^5$ represents an alkyl group, $R^{1B}$ and $R^{1C}$ each independently represent an oxygen atom or $NR^{102}$, $R^{102}$ represents a hydrogen atom or an alkyl group, b and c each independently represent an integer of 1 to 5, b and c satisfy 2≤b+c≤6, $L^3$ represents a (b+1)-valent aliphatic hydrocarbon group which contains a urethane bond or a urea bond and may contain —O—, $L^4$ represents a (c+1)-valent aliphatic hydrocarbon group which contains a urethane bond or a urea bond and may contain —O—, $L^5$ represents an alkylene group which may contain —O—, —$NR^{204}$—, —CO—, or a divalent linking group obtained by combining these, $R^{204}$ represents a hydrogen atom or a substituent, and $A^2$ represents S=O or a carbon atom.

5. A cured product formed by curing the curable composition according to claim 1.

6. The cured product according to claim 5 that is in the form of a film.

7. The cured product according to claim 5 that is a biomaterial.

8. A medical member comprising:
a substrate; and
the cured product according to claim 5 disposed on the substrate.

9. A compound represented by Formula (1),

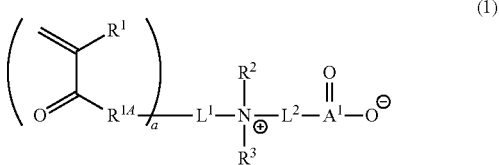

in the formula, $R^1$ represents a hydrogen atom or an alkyl group, $R^2$ and $R^3$ each independently represent an alkyl group, $R^{1A}$ represents an oxygen atom or $NR^{101}$, $R^{101}$ represents a hydrogen atom or an alkyl group, a represents an integer of 2 to 6, $L^1$ represents an (a+1)-valent aliphatic hydrocarbon group which contains a urethane bond or a urea bond and may contain —O—, $L^2$ represents an alkylene group which may contain —O—, —$NR^{104}$—, —CO—, or a divalent linking group obtained by combining these, $R^{104}$ represents a hydrogen atom or a substituent, and $A^1$ represents S=O or a carbon atom.

10. A compound represented by Formula (2),

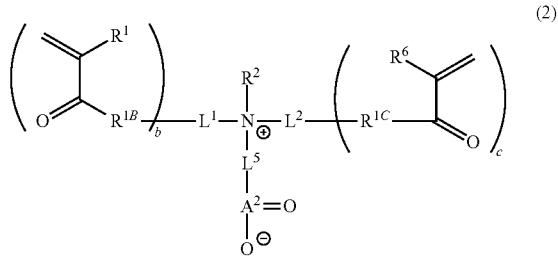

in the formula, $R^4$ and $R^6$ each independently represent a hydrogen atom or an alkyl group, $R^5$ represents an alkyl group, $R^{1B}$ and $R^{1C}$ each independently represent an oxygen atom or $NR^{102}$, $R^{102}$ represents a hydrogen atom or an alkyl group, b and c each independently represent an integer of 1 to 5, b and c satisfy 2≤b+c≤6, $L^3$ represents a (b+1)-valent aliphatic hydrocarbon group which contains a urethane bond or a urea bond and may contain —O—, $L^4$ represents a (c+1)-valent aliphatic hydrocarbon group which contains a urethane bond or a urea bond and may contain —O—, $L^5$ represents an alkylene group which may contain —O—, —$NR^{204}$—, —CO—, or a divalent linking group obtained by combining these, $R^{204}$ represents a hydrogen atom or a substituent, and $A^2$ represents S=O or a carbon atom.

* * * * *